United States Patent [19]

Vcelka

[11] Patent Number: 4,891,134
[45] Date of Patent: Jan. 2, 1990

[54] SAMPLE FILTRATION DEVICE

[75] Inventor: John L. Vcelka, Zion, Ill.

[73] Assignee: Abbott Laboratories, Abbott Park, Ill.

[21] Appl. No.: 148,260

[22] Filed: Jan. 25, 1988

[51] Int. Cl.$^4$ .............................................. B01D 33/00
[52] U.S. Cl. .................................... 210/359; 210/518; 422/101
[58] Field of Search ................. 210/359, 518; 422/101; 264/248, 336; 156/218, 308.4; 215/249

[56] References Cited

U.S. PATENT DOCUMENTS

| | | | |
|---|---|---|---|
| 3,325,576 | 6/1967 | Kessler | 264/336 |
| 3,481,477 | 12/1969 | Farr | 210/359 |
| 3,512,940 | 5/1970 | Shapiro | 422/101 |
| 3,693,804 | 9/1972 | Grover | 210/359 |
| 3,969,250 | 7/1976 | Farr | 210/359 |
| 3,970,565 | 7/1976 | Ahlstrand et al. | 210/359 |
| 4,035,150 | 7/1977 | Jaffe | 210/359 |
| 4,286,640 | 9/1981 | Knox et al. | 215/249 |
| 4,454,231 | 6/1984 | Cais et al. | 436/500 |
| 4,456,690 | 6/1984 | Cais et al. | 436/500 |
| 4,568,083 | 2/1986 | Miller | 264/248 |
| 4,800,020 | 1/1989 | Savas et al. | 210/359 |

Primary Examiner—Richard V. Fisher
Assistant Examiner—Cynthia Nessler
Attorney, Agent, or Firm—Thomas D. Brainard

[57] ABSTRACT

The present invention relates to a sample filtration device of the type employing differential pressure. An outer container filled with a sample to be filtered slidably receives a hollow plunger having filter media disposed near one end and sealing means disposed in an annular groove about the periphery of the plunger. The annular groove of the plunger is formed by two components: an annular shoulder on a collector portion and the axial face of an annular ring formed in a retainer portion. The two portions are frictionally engaged to retain the filter in place and form the annular groove for the sealing means. This construction permits straight-pull molding of the component parts which eliminates mold mismatch flaws.

5 Claims, 2 Drawing Sheets

SAMPLE FILTRATION DEVICE

BACKGROUND OF THE INVENTION

This invention relates to differential pressure filtration devices and, in particular, to a differential filtration device having an improved design which permits manufacturing with straight-pull molds and without mold mismatch flaws which arise from side action molds and can cause leakage.

Filtration devices employing differential pressure have been previously described in many patents. See, for example, Farr U.S. Pat. No. 3,481,477; Grover U.S. Pat. No. 3,693,804; Farr U.S. Pat. No. 3,969,250; Ahlstrand et al. U.S. Pat. No. 3,970,565; and Jaffe U.S. Pat. No. 4,035,150.

A typical prior art device (FIGS. 1 and 2) includes an outer container (a) which slidably receives a hollow plunger (b). A filter (c) is disposed near the end of the hollow plunger (b) and is retained there by a retainer ring (d) ultrasonically welded to the inside of the hollow plunger (b). Typically, an O-ring (e) is disposed in an annular groove (f) circumscribing the hollow plunger (b). The annular groove (f) is bounded and defined by shoulder portions (g) and (h) of increased diameter which prevent the O-ring (e) from moving with respect to the hollow plunger (b).

A major drawback of filtration devices of this type is the inability to manufacture them on straight-pull molds due to the annular groove (f) which makes it impossible to remove this part from a straight-pull mold. Consequently, previously known filtration devices have been manufactured in side action or two-part mold cavities divided longitudinally in half. As a result of two-part molds, mismatches known as parting lines (s) are inevitable along the seam joining the two halves. Even though mismatch flaws may only be on the order of a few thousandths of an inch, this can be enough to cause the O-ring (e) to seat improperly in the annular groove (f) and cause a leak. While flaws of this magnitude generally will not permit liquids to pass, they often will permit air to pass, causing a poor seal. A poor air seal compromises the pressurization of trapped air essential to good sample filtrate delivery in differential filtration devices.

In addition, heat generated by the ultrasonic welding of the retaining ring (d) to the end of the hollow plunger (b) can often damage the filter (c) which is adjacent thereto. Moreover, the pressure with which the ring (d) compresses the filter (c) cannot be adequately controlled. Insufficient or non-uniform pressure permits bypass leaks, while excessive pressure can damage the filter.

SUMMARY OF THE INVENTION

The present invention overcomes these disadvantages of the prior art filtration devices by providing a sample filtration device manufactured on straight-pull molds to avoid mismatch flaws associated with the prior art devices. The invention also overcomes the disadvantages of ultrasonic welding by providing friction means for retaining the filter media within the core of the hollow plunger.

In one aspect, the present invention comprises an improved differential pressure sample filtration apparatus. An outer container, closed at one end for holding a fluid sample for filtering. slidably receives a hollow plunger. The hollow plunger comprises two pieces: a first piece or collector portion having an annular shoulder thereon; and a second piece or retaining portion having a first annular ring. The retaining portion is affixed to the collector portion such that the annular shoulder of the collector portion and the first annular ring of the retaining portion cooperate to form the sides of an annular groove which retains a sealing means. The sealing means may comprise any structure capable of achieving a fluid seal between the outer container and the hollow plunger, for example, an O-ring or flat washer. A filtering means is disposed near one end of the plunger for filtering fluid from the outer container into an inner collecting means in the hollow plunger, as the plunger is inserted into the outer container.

Preferably, the retaining portion also includes a plurality of legs connecting the first annular ring to a second annular ring which is smaller in diameter and axially spaced from the first annular ring. The second annular ring is dimensioned to fit inside the hollow portion of the plunger to retain the filter media in place. Ideally, the retaining portion is affixed to the collector portion by means of friction fit or "snap fit" between the second annular ring and the interior of the hollow plunger.

In another aspect, the invention comprises a method for forming and assembling the components of the filtration device using straight pull molds, which method eliminates leaking due to parting line mismatch flaws. According to the method of the invention, a collector portion of the plunger and a retaining portion of the plunger are formed separately, each from a distinctly configured straight pull mold, and are assembled so that an annular shoulder on the collector portion cooperates with an annular face on the retaining portion to form the annular groove in which the sealing means is disposed. Preferably, the retaining portion and the collector portion remain engaged due to friction between a second annular ring dimensioned to frictionally engage the interior of the collector portion.

BRIEF DESCRIPTION OF THE DRAWINGS

A better understanding of the invention can be had by reference to the following detailed description of a preferred embodiment when read in conjunction with the accompanying drawings in which like reference numerals refer to like parts throughout the several views and in which.

DETAILED DESCRIPTION OF THE PREFERRED EMBODIMENT

Figure 3:
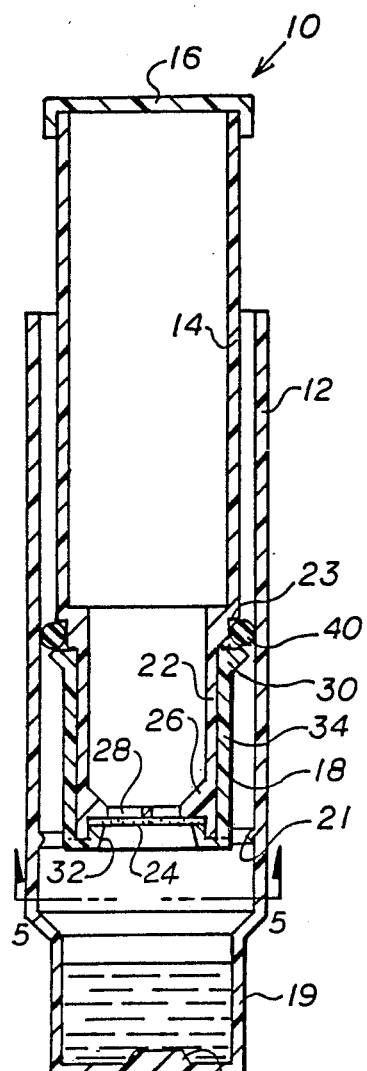
FIG. 3 is a longitudinal cross-sectional view of the filtration device of the present invention.

In FIG. 3, the filtration device 10 is depicted in longitudinal cross-section and comprises a cylindrical outer container 12 into which is slidably received a cylindrical, hollow plunger. The hollow plunger comprises a first piece or collecting portion 14, the upper end of which (as viewed in FIGS. 3 and 4) is closed by a cap 16. A second piece of the plunger, a retaining portion 18 (somewhat resembling and herein referred to as a "crown"), is shown at the opposite end of the collector portion 14.

Figure 5:
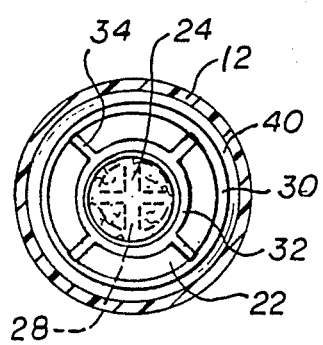
FIG. 5 is a cross sectional view taken substantially along line 5—5 of FIG. 3.

As shown in FIGS. 3 and 5, the outer container 12 comprises a cylindrical tube having inner and outer walls. The container 12 is open at a top end and closed at a bottom end. A section of the container 12 near the bottom end preferably includes a radially reduced portion 19 and the interior face of the bottom end includes a raised bump 20 for a reason to be subsequently discussed. Circumferentially spaced in the interior wall of the container 12, just above the reduced portion 19, are formed a plurality of raised nubs 21 which serve a purpose to be described below.

The collector portion 14 (FIGS. 3, 4 and 5) similarly comprises a cylindrical tube but is open at both ends to form a hollow passageway or collecting chamber in the interior of the plunger. The exterior of the lower or inserted end (as viewed in FIGS. 3 and 4) of the collector piece 14 also has a reduced diameter portion 22 forming an annular shoulder 23. The interior lower end of the collector portion 14 houses filter media 24 and may or may not have a correspondingly reduced portion.

The filter media 24 may be single or multiple layer and comprises any known filtering media including, but not limited to, paper, glass fiber, cellulose, and nitrocellulose. Depth filters are generally preferred over membrane filters due to their ability to remove greater quantities of particulate matter without becoming occluded. Especially preferred for most applications is fiberglass combined with polypropylene, however, different media may be preferred, depending on the application.

The filter media 24 is held in place from above by an annular ledge 26 formed in the interior walls of the collector portion 14 and, optionally, by cross bars 28 extending diametrically across the opening formed by the annular ledge 26. The annular ledge 26 and, if necessary, the cross bars 28 support the filter media 24 against the pressurized sample which must be filtered as the plunger is inserted into the outer container 12.

Figure 4:
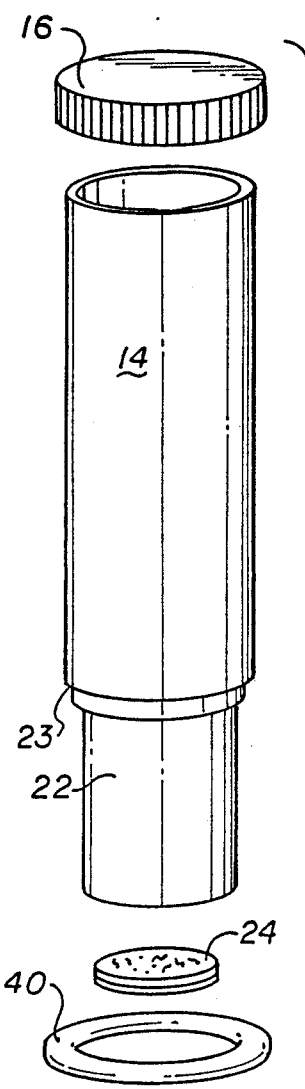
FIG. 4 is an exploded perspective view of the plunger portion of the invention.
Figure 6:
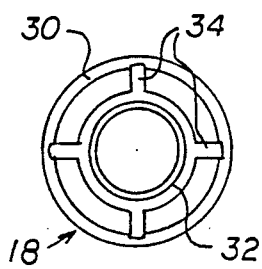
FIG. 6 is a bottom plan view of the retaining portion of the plunger.

From below, the filter media 24 is supported by the retaining portion or crown 18. As best shown in FIGS. 4 and 6, the crown 18 comprises a first annular ring 30 and a second annular ring 32 which are joined together by a plurality of longitudinal legs 34. The first annular ring 30 is larger in diameter and is dimensioned to fit snugly over the reduced diameter portion 22 of the collector piece 14. Conversely, the second annular ring 32 is smaller in diameter and is dimensioned to fit snugly inside the interior wall of the reduced portion 22 of the collector piece 14. Accordingly, the legs 34 are somewhat L-shaped. As best seen in FIGS. 3 and 4, the legs 34 axially space the second annular ring 32 from the first annular ring 30 which gives the crown 18 its characteristic appearance. Furthermore, the second annular ring 32 includes a portion that extends axially upward from the foot of the leg 34 so that it can be inserted into the hollow interior of the reduced diameter portion 22 of the collector portion 14 to retain the filter media 24 in position. Preferably, circumferentially spaced raised nubs 33 are disposed on either the outside of the second annular ring 32 (see FIG. 4) or the inside of the reduced portion 22 below the annular ledge 26 (not shown). The other component (ring 32 or inside of portion 22) has depressions (not shown) corresponding to the nubs 33 to securely lock one to the other.

As best seen in FIG. 3, the legs 34 have a length slightly less than the axial length of the reduced diameter portion 22 which leaves a gap between the top axial face 36 of the first annular ring 30 and the annular shoulder 23 formed by the reduced portion 22 of the collector piece 14. The gap defines an annular groove about the periphery of the plunger into which an O-ring 40 is securely seated. In this manner, the O-ring 40 slides with the plunger as it is inserted into the outer container 12 so that a fixed quantity of air is trapped in the outer container 12 and forces the sample through the filter media 24.

While the preferred embodiment of the crown 18 has been described, the invention also contemplates other straight-pull molded retaining portions secured to a collector portion 14 by suitable means and having an annular face axially spaced from the annular shoulder 23 to form an annular groove. A second ring, distinct or continuous with the retaining portion, can optionally form the filter retaining means.

Figure 1:
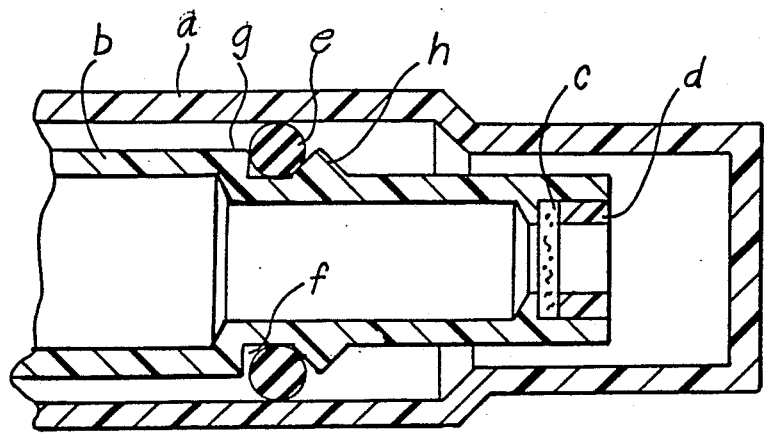
FIG. 1 is a longitudinal cross-section of a filtration device known in the prior art.
Figure 2:
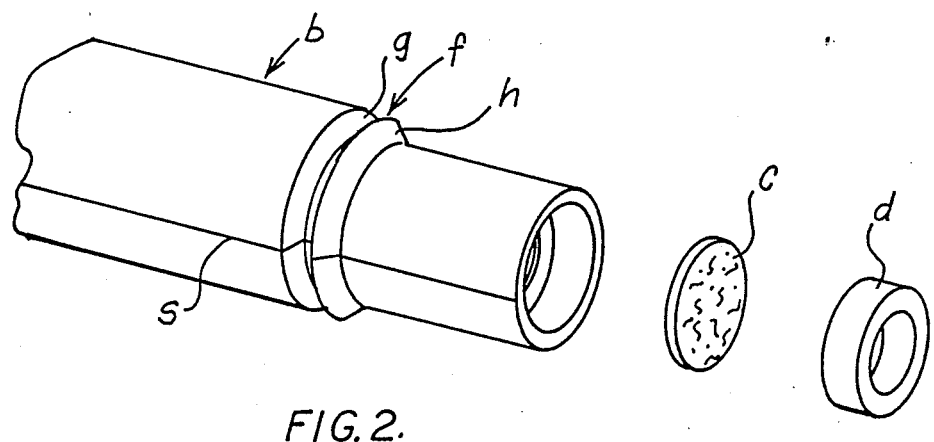
FIG. 2 is an exploded perspective view of the plunger portion of the filtration device of FIG. 1.

It will be apparent to those skilled in the art that the gap between the annular shoulder 23 and the top axial face 36 is equivalent in function to the annular groove (f) of the prior art defined by the raised portions (g) and (h) as shown in FIGS. 1 and 2. However, by forming the cap from two components (ie. the collector portion 14 and the crown portion 18 of the plunger), it is possible to achieve the filtration device 10 which can be molded from straight-pull molds to eliminate mismatch flaws or parting lines inherent in two-piece or side action molds. By eliminating these mismatch flaws, it is possible to decrease the chances that a particular plunger will have an air leak past the O-ring 40.

Each of the major components of the device 10, namely the outer container 12, the collector piece 14 and the crown 18, is made of a relatively rigid substance such as plastic, polypropylene or polyethylene. These components may all be made of the same material. An especially preferred substance is polypropylene because it is easily molded by injection molding techniques and relatively inert to the assay. Ideally, the material is flexible enough and the dimensions small enough to permit the nubs 21 to be formed in spite of the shear action of the mold.

A typical mold (FIG. 7) for forming the collector portion 14 of the plunger comprises a cavity 50 cut into a block 52. The cavity 50 is dimensioned to correspond to the outer wall of the collector portion and is open at the top. The bottom of the cavity 50 can be formed by the block 52, but more conveniently is formed by a pin 53 inserted into the cavity 50 to a predetermined position. The block 52 also has a port or gate 54 opening between the cavity 50 and a source 56 of molten plastic to permit injection molding of the component. A core 58 is inserted into the center of the cavity 50 and is dimensioned to correspond with the interior dimensions of the collector portion 14. The core 58 is centered within the cavity 50 by means of spacers 60 which also can be used to remove the formed collector piece 14 from the central core 58 by sharp downward pressure. The pin 53 is centered by a spacer plate or collar 62, which may be integral with the block 52 or separate.

Figure 7:
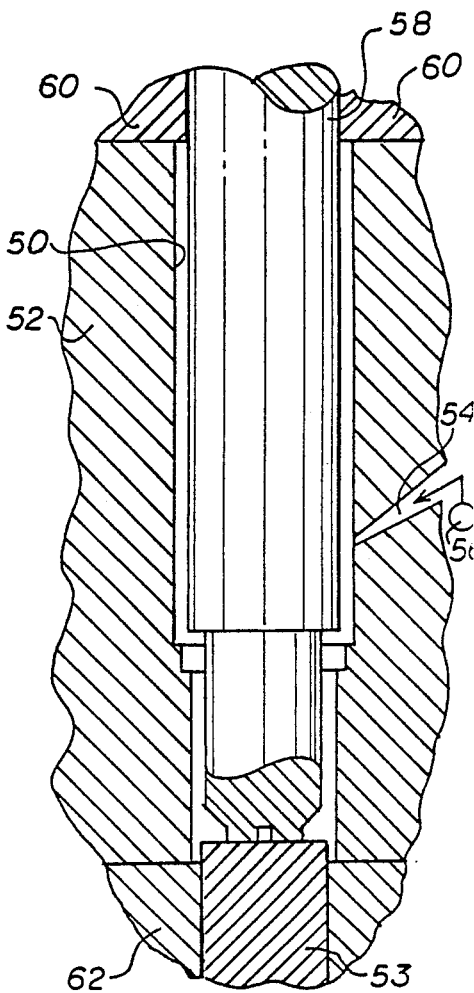
FIG. 7 is a diagrammatic representation of a straight-pull mold employed in the invention.

The crown 18 can be formed similarly from a straight-pull mold having a cavity and central core slightly different than those of FIG. 7 but which can easily be determined by one skilled in the art. The retaining portion or crown 18 is then slid over the reduced diameter portion 22 of the collector portion 14 and locked into place by frictional engagement of the nubs 33. The retainer portion forms part of the annular groove for the O-ring 40 and, simultaneously, holds the filter media 24 in place.

In use, a liquid sample to be filtered is placed in the bottom of the reduced diameter portion 20 of the outer container 12. The plunger is inserted filter end first into the open end of the outer container 12 and the O-ring 40 sealingly engages the inner wall to form an air-tight seal between the outer container 12 and the plunger 14. As the plunger is depressed further into the outer container 12, air is forced through the filter media 24 and escapes through the loosely fitting cap 16.

Once the plunger reaches the surface of the sample fluid to be filtered, a fixed quantity of air is trapped between the O-ring 40 and the fluid level and, upon further depression of the plunger this trapped air is compressed. The pressurized air in turn forces the fluid sample through the filter media 24 and into the collecting chamber in the interior of the hollow plunger. As the reduced diameter portion 22 of the plunger is pushed into the reduced diameter portion 20 of the outer container 12, the trapped quantity of air is forced into a smaller volume which multiplies its compressive effect on the fluid to deliver as much sample as possible through the filtering media 24. This arrangement increases the efficiency of filtration which is important for small volume samples.

The bump 20 at the bottom end of the outer container 12, by occupying space inside the second annular ring 32, also serves to decrease the available space for trapped air, thereby to deliver as much sample filtrate as possible.

Filtration is complete when the plunger hits the bottom end of the outer container 12. Simultaneously, the O-ring 40 snaps past the nubs 21 formed in the inner wall of container 12 to lock the two components together. This feature permits thick and thin samples alike to be filtered without the need for holding the components together manually. This is advantageous since some samples take longer than others to completely filter.

When filtration is complete, the filtrate can be poured from the open end of the hollow plunger upon removal of the cap 16. Alternatively, additional reagents can be added to the filtered sample in the inner collector portion to further process the sample prior to pouring. Filtered sample can then be poured into any desired assay format without including undesired particulate matter present in the original sample.

The foregoing description of the preferred embodiment has been given for purposes of illustration only and no unnecessary limitations should be understood therefrom. Rather, the invention is intended to be limited only by the following claims:

What is claimed is:

1. A differential pressure sample filtration device comprising:
   an outer container for receiving a liquid for filtering; and
   a hollow plunger dimensioned to be slidably received in said outer container and comprising:
      a first piece having at one end a reduced diameter portion forming an annular shoulder, means for collecting liquid filtrate and filter means disposed between said one end of the plunger and said means for collecting liquid filtrate; and
      a second piece having an annular axial face and being dimensioned to be secured to said first piece such that the annular axial face and the annular shoulder cooperate to form an annular groove about said plunger, said annular groove being adapted for receiving a sealing means for forming a liquid seal between the outer container and the hollow plunger, wherein said second piece comprises a first annular ring dimensioned to slidably fit over said one end of said first piece, a second annular ring dimensioned to slidably fit into the hollow portion of said one end of the first piece to abut said filter means, and a plurality of legs connecting said first annular ring to said second annular ring.

2. The device according to claim 1 wherein said first and second pieces of the plunger are lockingly engaged by friction.

3. The device according to claim 1 wherein the annular axial face includes a frusto-conical aspect.

4. In a sample filtration device of the differential pressure type having a hollow plunger slidable into an outer container of liquid to be filtered, a filter disposed in one end of said plunger, and sealing means disposed in an annular groove about the plunger to sealably engage said outer container wall, the improvement comprising:
   a plunger having a collector portion and a retaining portion, wherein said collector portion includes an annular shoulder and said retaining portion includes a first annular ring dimensioned to slidably fit around said plunger, said annular shoulder and said annular ring defining said annular groove; and wherein said retaining portion further comprises a second annular ring dimensioned to slidably fit into said one end of the hollow plunger to abut said filter and leg means rigidly connecting said first and second annular rings.

5. The device according to claim 4 wherein said first annular ring includes a frusto-conical face.

* * * * *